US00PP33860P2

(12) United States Plant Patent
Van Swieten

(10) Patent No.: US PP33,860 P2
(45) Date of Patent: Jan. 11, 2022

(54) ***PHALAENOPSIS* ORCHID PLANT NAMED 'PHA1566855'**

(50) Latin Name: ***Phalaenopsis* hybrid**
Varietal Denomination: PHA1566855

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,579

(22) Filed: Aug. 25, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHA1566855', particularly characterized by having copper flowers with reddish-purple lips, flowers that are flat in lateral view, dorsal sepals with an incurving curvature of the longitudinal axis, medium curvature of the lateral lobes, and is propagated by meristem tissue culture, is disclosed.

3 Drawing Sheets

Genus and species: *Phalaenopsis* hybrid.
Variety denomination: 'PHA1566855'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA1566855'.

The new *Phalaenopsis* plant is a product of a planned breeding program conducted by the inventor in Bleiswijk, the Netherlands. The objective of this breeding program was to create a new *Phalaenopsis* plant with attractive copper flowers with reddish-purple lips, suitable for potted plant production.

The new *Phalaenopsis* plant 'PHA1566855' is a result of cross-pollination made by the inventor in March 2013 in Bleiswijk, the Netherlands, of the proprietary female, or seed parent, *Phalaenopsis* hybrid '44437-04' (unpatented) with the proprietary male, or pollen parent, *Phalaenopsis* hybrid '01-3705' (unpatented).

The new *Phalaenopsis* was selected by the inventor as a single plant within the progeny of the stated cross-pollination in a controlled greenhouse in Bleiswijk, the Netherlands, in December 2015. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 22, 2020 (Application no. 2020/2290), by Applicant who obtained the subject matter disclosed directly from the inventor. 'PHA1566855' has not been made publicly available or sold anywhere in the world prior to the effective filing date of this application with the exception of sales or disclosures made one year or less before the effective filing date of this claimed invention by Applicant who obtained 'PHA1566855' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA1566855' as a new and distinct variety of *Phalaenopsis* plant:

1) Copper flowers with reddish-purple lips;
2) Flower shape in lateral view is flat;
3) Curvature of longitudinal axis of dorsal sepal is incurving; and
4) Curvature of lateral lobe is medium.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in June 2021. Colors in the photographs may differ from the color values cited in the detailed botanical description, which accurately describe the actual colors of the new variety.

DESCRIPTION OF THE NEW VARIETY

Figure 1:
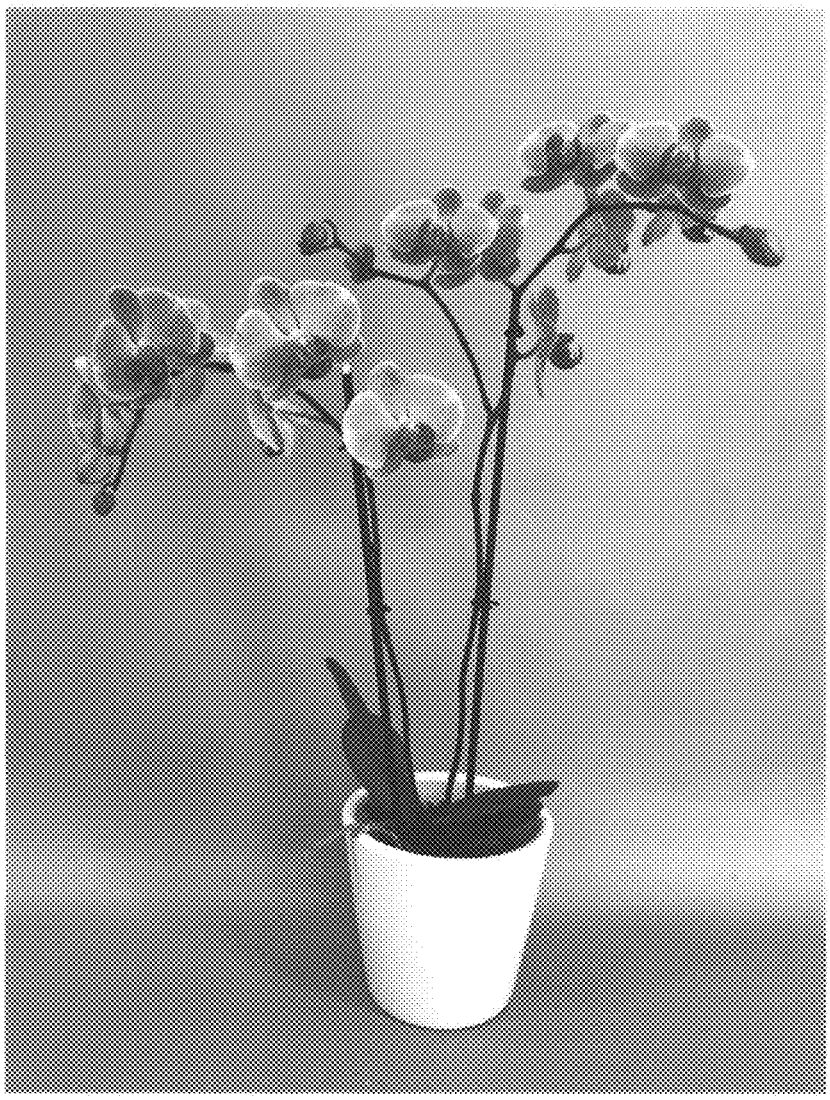
FIG. 1 shows the overall plant habit, including blooms, buds, and foliage of 'PHA1566855'.
Figure 2:
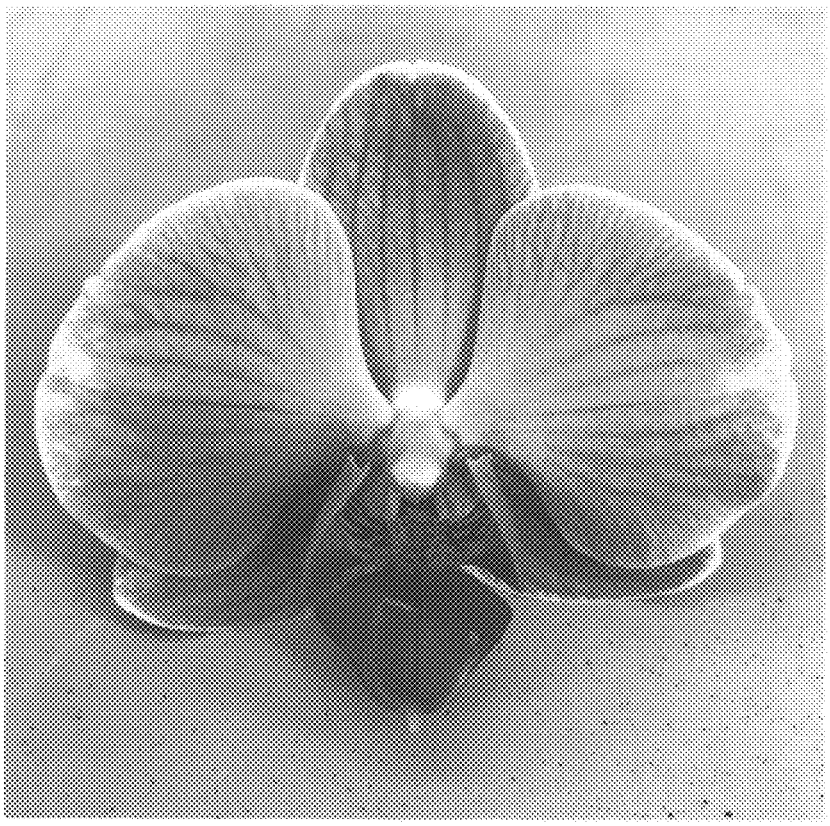
FIG. 2 shows a close-up of a flower of 'PHA1566855'.
Figure 3:
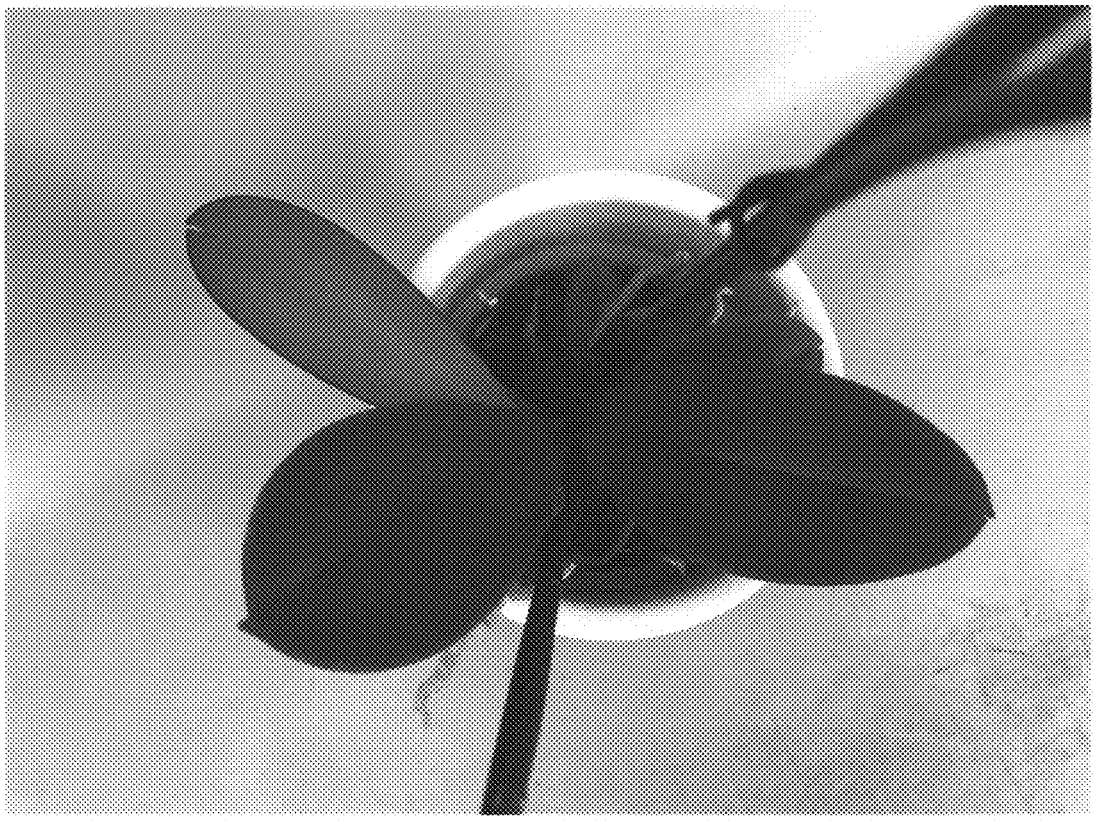
FIG. 3 shows an overhead view of the leaves of 'PHA1566855'.

The following detailed description sets forth the distinctive characteristics of 'PHA1566855'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in June 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA1566855'.

Parentage:

*Female parent*.—*Phalaenopsis* cultivar '44437-04' (unpatented).

*Male parent*.—*Phalaenopsis* cultivar '01-3705' (unpatented).

Propagation:

*Type*.—Meristem tissue culture.

Roots:

*Root description*.—Greyed-green (a color in between RHS 190B and RHS 190C) colored roots with branching lateral roots having yellow-green (RHS 144C) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 49.0 cm to 59.0 cm.

*Width* (*measured from leaf tips*).—About 26.0 cm to 31.0 cm.

*Vigor*.—Strong.

Leaves:

*Mature leaves*.—Quantity per plant: 6 to 7 leaves are produced before flowering. Length (fully expanded): 13.0 cm to 16.0 cm. Width: 5.0 cm to 6.0 cm. Position of the broadest part of the leaf: At the middle. Shape: Oblong. Base shape: Moderately elongated. Apex: Obtuse asymmetric. Leaf blade angle with the petiole (measured from the horizontal position): Between 10 degrees and 30 degrees. Leaf margin: Entire. Color: Upper surface: RHS 146A. Lower surface: RHS 146B with purple overcolor and margins (RHS N77A). Texture (both upper and lower surfaces): Smooth. Thickness: 1.8 mm to 2.2 mm. Variegation: Absent. Venation: Pattern: Parallel. Color of the midvein: Upper surface: Mix of green (RHS 147A) and dark reddish-brown (RHS 200A). Lower surface: Green (RHS 146B) with a touch of purple (RHS N77A).

Peduncle:

*Quantity per plant*.—1 to 2.

*Number of flowers per peduncle*.—10 to 20.

*Length*.—49.0 cm to 59.0 cm.

*Diameter*.—3.0 mm to 4.0 mm.

*Strength*.—Strong.

*Aspect*.—Upright to slightly pendent.

*Texture*.—Smooth.

*Color*.—Dark reddish-brown-purple (a color in between RHS 200A and RHS N77A) with a hint of green (RHS 146D).

*Internode length*.—3.0 cm to 4.0 cm.

Inflorescence description:

*Appearance*.—Upright to slightly pendent, panicle inflorescence with bilaterally symmetrical flowers that open in succession beginning with the lowermost flower.

*Number of inflorescences*.—1 to 2.

*Inflorescence size*.—Height (from base to tip): 240.0 mm to 340.0 mm.

*Flowering time*.—First flowers can be expected 10 to 11 months after planting in a 12-cm pot.

*Flower*.—Height: 60.0 mm to 65.0 mm. Diameter: 75.0 mm to 80.0 mm. Depth of lip: 20.0 mm to 22.0 mm.

*Flower shape*.—Flat.

*Flower longevity*.—On the plant: 7 to 9 weeks.

*Fragrance*.—Absent.

*Flower bud*.—Average size: Medium. Length: 18.0 mm to 20.0 mm. Width: 17.0 mm to 19.0 mm. Shape: Egg shaped. Color: Greenish-yellow (RHS 151A) with purplish-red stripes (RHS N77B).

*Petals*.—Arrangement: Open/free. Shape: Semi-circular. Apex: Emarginated asymmetric. Margin: Moderately undulated. Length (from base to tip): 34.0 mm to 36.0 mm. Width: 41.0 mm to 43.0 mm. Position of the broadest part of the petal: Toward the base. Color (when fully opened): Upper surface: Basic color: Light greenish-yellow (a color in between RHS 4B and RHS 4C). Over color: Touch of purplish-pink (RHS N78C) at the base; purplish-red stripes (RHS 184C); reddish-orange shade (RHS 174C). Lower surface: Basic color: Light greenish-yellow (RHS 4C). Over color: Light purple (RHS 76A); diluting stripes (RHS 186A); pink shade (RHS 182C). Number of spots and stripes on the petals (upper surface): Medium stripes. Color of spots and stripes on the petals (upper surface): RHS 184C. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 35.0 mm to 37.0 mm. Width: 26.0 mm to 28.0 mm. Position of the broadest part of the dorsal sepals: At the middle. Color (when fully opened): Upper surface: Basic color: Light greenish-yellow (RHS 4C). Over color: Touch of purplish-red (RHS 60C) at the base and purplish-red stripes (RHS 184C) and netting (RHS 184D); reddish-orange shade (RHS 174B). Lower surface: Basic color: Light greenish-yellow (RHS 4C). Over color: Greenish-yellow shade (RHS 151A); dark pink stripes (RHS 182C) toward margins. Number of spots and stripes on the dorsal sepals (upper surface): Medium stripes. Color of spots and stripes on the dorsal sepals (upper surface): RHS 184C. Density of netting of the dorsal sepals (upper surface): Low. Color of the netting: RHS 184D.

*Lateral sepals*.—Shape: Ovate. Apex: Obtuse asymmetric. Margin: Weakly undulated. Length (from base to tip): 35.0 mm to 37.0 mm. Width: 24.0 mm to 26.0 mm. Position of the broadest part of the lateral sepals: Toward the base. Color (when fully opened): Upper surface: Basic color: Light greenish-yellow (RHS 4B). Over color: Purplish-red dots (RHS 59B) at the base; red shade (RHS 181B) at the middle; lighter red shade (RHS 181C) toward margins; purplish-red stripes (RHS 59C) and netting (RHS 184C). Lower surface: Basic color: Greenish-yellow (RHS 151A). Over color: Diluting purplish-red stripes (RHS 186A). Number of spots, dots, and stripes on the lateral sepals (upper surface): Few to medium very small dots at the base; medium stripes. Color of spots, dots, and stripes on the lateral sepals (upper surface): Dots (RHS 59B); stripes (RHS 59C). Density of netting of the lateral sepals (upper surface): Medium. Color of the netting (upper surface): RHS 184C.

*Labellum* (*lip*).—Whiskers: Present. Length of whiskers: 10.0 mm to 12.0 mm. Color of whiskers: Reddish-purple (RHS N78A) on one side; purplish-red (RHS 60B) toward the other side; small yellow tips (RHS 9A). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated (widely wavy). Length: 19.0 mm to 21.0 mm. Width: 12.0 mm to 14.0 mm. Color: Upper surface: Touch of yellow (RHS 9B) and yellowish-white (RHS 156D) with dark red stripes (RHS 59A) at the base; red (RHS 185A) on one side and reddish-purple (RHS N78B) toward the other side; light reddish-purple (RHS N78D) toward the tip. Lower surface: Yellowish-white (RHS 156D) at the base; red (RHS 185A) on one side; reddish-purple (RHS 70B) at the middle; light reddish-purple (RHS N78D) toward the tip. Number of spots and stripes on the lateral lobe: Few to medium stripes. Color of spots and stripes on the lateral lobe: RHS 59A. Density of netting of the lateral lobe: None. Color of the netting: Not applicable.

*Apical lobe*.—Shape: Triangular. Margin: Entire. Length: 18.0 mm to 20.0 mm. Width: 19.0 mm to 21.0 mm. Color: Upper surface: Touch of yellow (RHS 9B) at the base; purplish-red (RHS 59B and RHS 60B) from base toward whiskers; red wings (RHS 185A). Lower surface: Light yellow-green (RHS 157C) at the middle from base toward whiskers; red wings (RHS 185A); lighter red (RHS 185B) toward whiskers; reddish-purple (RHS N78B) on sides toward whiskers. Number of spots and stripes on the apical lobe: None. Color of spots and stripes on the apical lobe: Not applicable. Density of netting of the apical lobe: None. Color of the netting: Not applicable.

*Callus*.—Average size: Medium. Height: 5.0 mm to 6.0 mm. Length: 6.0 mm to 7.0 mm. Width: 3.0 mm to 4.0 mm. Color: Yellow (RHS 9C) on sides; yellow tips (RHS 9B); spotted (RHS 183A).

Reproductive organs:

*Column*.—Length: 9.0 mm to 11.0 mm. Diameter: 4.8 mm to 5.3 mm. Color: Light reddish-purple (RHS N78D).

*Pollinia*.—Quantity: 2. Diameter: 0.8 mm to 1.0 mm. Color: Orange (RHS N25B).

*Ovary*.—Length: 12.0 mm to 14.0 mm. Diameter: 2.4 mm to 2.6 mm.

*Pedicel*.—Length: 36.0 mm to 38.0 mm. Diameter: 2.7 mm to 3.0 mm. Color: Light yellow-green (RHS 145B) at the base; lighter yellow-green (RHS 145C) with a touch of pinkish-white (RHS N155C) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA1566855' differs from the female parent plant '44437-04' (unpatented) in that 'PHA1566855' has triangular apical lobes, flowers with a main color of light greenish-yellow, and a normal lip size, whereas '44437-04' has trapezoid apical lobes, flowers with a main color of purplish-pink, and an extra-large lip size.

'PHA1566855' differs from the male parent plant '01-3705' (unpatented) in that 'PHA1566855' has triangular apical lobes, emarginated petal apexes, and flowers with a main color of light greenish-yellow, whereas '01-3705' has ovate apical lobes, rounded petal apexes, and flower with a main color of yellow.

'PHA1566855' is most similar to the commercial *Phalaenopsis* plants named 'PHALJALZE' (U.S. Plant Pat. No. 33,553) and 'PHALIFQUDI' (U.S. Plant Pat. No. 26,831). 'PHA1566855' differs from the commercial variety 'PHALJALZE' in that 'PHA1566855' has flowers that are flat in lateral view, whereas 'PHALJALZE' has flowers that are convex in lateral view. Additionally, 'PHA1566855' has smaller flowers, narrower leaves, and narrower petals than 'PHALJALZE'.

'PHA1566855' differs from the commercial variety 'PHALIFQUDI' in that 'PHA1566855' has flowers that are flat in lateral view, whereas 'PHALIFQUDI' has flowers that are concave in lateral view. Additionally, 'PHA1566855' has narrower leaves and narrower peduncles than 'PHALIFQUDI'.

I claim:

1. A new and distinct variety of *Phalaenopsis* plant named 'PHA1566855', substantially as described and illustrated herein.

* * * * *